United States Patent [19]

Hill et al.

[11] Patent Number: 5,150,171
[45] Date of Patent: Sep. 22, 1992

[54] FLUXES SCINTILLOMETER

[75] Inventors: Reginald J. Hill, Boulder; Gerard R. Ochs, Longmont, both of Colo.

[73] Assignee: The United States of America as represented by the Secretary of Commerce, Washington, D.C.

[21] Appl. No.: 559,039

[22] Filed: Jul. 30, 1990

[51] Int. Cl.$^5$ .................. G01N 21/41; G01M 9/00
[52] U.S. Cl. .................. 356/128; 73/147; 73/861.06
[58] Field of Search .............. 73/861.06, 147, 189, 73/662, 866.4, 23.2, 154; 250/574, 253; 356/128, 129, 336, 338

[56] References Cited

U.S. PATENT DOCUMENTS

| | | | |
|---|---|---|---|
| 3,623,361 | 11/1971 | Funk, Jr. | 73/147 |
| 3,889,533 | 6/1975 | Balser . | |
| 4,099,878 | 7/1978 | Lee | 356/128 |
| 4,286,462 | 9/1981 | Bourne . | |
| 4,385,830 | 5/1983 | Webb et al. . | |
| 4,613,938 | 9/1986 | Hansen et al. . | |
| 4,654,803 | 3/1987 | Sell | 356/128 |
| 4,760,743 | 8/1988 | Clifford et al. . | |
| 4,890,488 | 1/1990 | Pincent et al. . | |
| 4,920,793 | 5/1990 | Djorup . | |

OTHER PUBLICATIONS

Journal of the Optical Society of America (vol. 62, No. 5, 1972) Laser Remote Sensing of Atmospheric Refractive Index Fluctuation Profile.

Applied Optics (Nov. 1970, vol. 9, No. 11) "Investigation of Atmospheric Turbulence by Narrow Laser Beams", Ronchi, et al.

IBM Technical Disclosure Bulletin (vol. 21, No. 10, 1979) "Trace Analysis in gases by laser-induced Schlieren Technique".

G. R. Ochs et al., "A Refractive-Index Structure Parameter Profiling System," NOAA Technical Memo ERL WPL-161, Feb. 1989.

G. R. Ochs et al., "Finite Aperture Optical Scintillometer for Profiling Wind and $C_n^2$," Appl. Opt. 17, (1978), pp. 3774–3778.

Ochs et al., "An Optical Inner-Scale Meter," NOAA Technical Memorandum, ERL WPL-183, Sep. 1990.

Kohsiek, "Measuring *, *, and $C_{TQ}$ in the Unstable Surface Layer and Relations to the Vertical Fluxes of Heat and Moisture," Boundary-Layer Meteorology, No. 24 (1982), pp. 89–107.

Wyngaard et al., "Behavior of the Refractive-Index-Structure Parameter near the Ground," Journal of the Optical Society of America, vol. 61, No. 12, Dec. 1971, pp. 1646–1650.

Wyngaard et al., "The Budgets of Turbulent Kinetic Energy and Temperature Variance in the Atmospheric Surface Layer," Journal of the Atmospheric Sciences, vol. 28, Mar. 1971, pp. 190–201.

J. Tant Priestley, "Data Acquisition and Analysis for the 1988 Micrometeorological Scintillation Experiment," NOAA Technical Memorandum ERL WPL-170, Aug. 1989.

J. Tant Priestley, "An Operator's Manual for Fluxes Scintillometer Software with Design Recommendations for an Integrated System," NOAA Technical Memorandum ERL WPL-178, Mar. 1990.

(List continued on next page.)

Primary Examiner—Richard A. Rosenberger
Assistant Examiner—Hoa Pham
Attorney, Agent, or Firm—Lowe, Price, LeBlanc & Becker

[57] ABSTRACT

A laser scintillometer measures the variance of the log intensity of diverged laser light received via a first path. A large aperture scintillometer measures the variance of the log intensity of light from an incoherently illuminated source received via a second path. The ratio of the two measured variances gives the inner scale of turbulence. The refractive-index structure parameter is derived from either measured variance and the inner scale. A processor then derives values of fluxes, such as heat flux and momentum flux, from the refractive-index structure parameter and the inner scale of turbulence using Monin-Obukhov similarity relationships.

19 Claims, 4 Drawing Sheets

OTHER PUBLICATIONS

R. J. Hill et al., "Optical Scintillation Instruments for Measuring Heat and Momentum Fluxes in the Atmospheric Surface Layer," *Digest of the Topical Meeting on Remote Sensing of the Atmosphere*, Feb. 12–15, 1990, Hyatt Lake Tanoe, Incline Village, Nev., pp. 1–4.

R. J. Hill et al., "Surface-Layer Meteorology by Optical Scintillation Techniques," *Optical Techniques for Remote Probing of the Atmosphere: Technical Digest;* Jan. 10–12, 1983, pp. TuC16-1 to TuC16-4.

G. R. Ochs et al., "An optical device for path-averaged measurements of $C_n^2$," *SPIE*, vol. 277, Atmospheric Transmission (1981), pp. 2–5.

Hill et al., "Fine calibration of large-aperture optical scintillometers and an optical estimate of inner scale of turbulence," *Applied Optics*, vol. 17, No. 22, Nov. 15, 1978, pp. 3608–3612.

J. C. Wyngaard, "An Optical Heat Flux Experiment," *Fourth Symposium on Meteorological Observations and Instrumentation*, Apr. 10–14, 1978.

Wang et al., "A saturation-resistant optical scintillometer to measure...," *J. Opt. Soc. Am.*, vol 68, No. 3, Mar. 1978, pp. 334–338.

P. M. Livingston, "Proposed Method of Inner Scale Measurement in a Turbulent Atmosphere," *Applied Optics*, vol. II, No. 3, Mar. 1972, pp. 684–687.

Thiermann et al., "Modeling of structure constant and inner scale of refractive index fluctuation-an experimental investigation," Technical Paper of Forschungsinstitut für Optik, Tübingen, W. Germany.

Ochs et al., "Optical-scintillation method of measuring turbulence inner scale," *Applied Optics*, vol. 24, No. 15, Aug. 1, 1985, pp. 2430–2432.

R. J. Hill "Comparison of scintillation methods for measuring the inner scale of turbulence," *Applied Optics*, vol. 27, No. 11, Jun. 1, 1988, pp. 2187–2193.

//<br>
FLUXES SCINTILLOMETER

TECHNICAL FIELD

This invention relates to an optical instrument which measures the path averaged heat and momentum fluxes of the atmosphere.

BACKGROUND ART

The atmospheric surface layer extends from the ground to a few tens of meters in height. The surface layer is unstable if heat is rising from the ground, as is common during sunshine. The rising heat adds to the turbulence. The surface layer is stable if the ground is cooler than the air so that heat is transferred downward, as is common at night. Such stability tends to damp turbulence. The surface layer is near neutral if wind shear produces almost all of the turbulence, whereas the heat transfer between ground and air is not effective in producing or damping turbulence. This condition typically occurs when the wind is strong and/or solar radiation is weak. Heat flux is the vertical transport (rising or descending) of heat from or to the ground. Momentum flux (always downward) is the effect of the frictional drag of the ground on the wind blowing over it.

Temperature fluctuations in the air cause the scintillation (twinkling) of distant light sources. The strength of these temperature fluctuations at the spatial scales (10 cm to 1 mm) that produce scintillation is represented by the refractive-index structure parameter, which is denoted by $C_n^2$. The smallest spatial size of temperature fluctuations is represented by the inner scale of turbulence, denoted by $l°$. Horizontal homogeneity means that the average quantities (as opposed to instantaneous turbulence fluctuations) are the same everywhere in a horizontal plane to within distances of several hundred times the height above ground; examples of such average quantities are heat flux, momentum flux, average wind speed, $C_n^2$, and $l°$. For the horizontally homogeneous atmospheric surface layer there are empirical relationships between the fluxes of heat and momentum and the parameters $C_n^2$ and $l°$. The discussion below refers to this horizontally homogeneous case.

A variety of in situ techniques are known for measuring atmospheric fluxes. The prior art methods of measuring fluxes include using a sonic anemometer or performing indirect-dissipation measurements using a fine wire thermometer and hot-film anemometers. These prior art methods, however, require excessive processing and high data rates. Also, the instruments are not particularly rugged. For example, fine-wire thermometers are subject to hygroscopic-particle contamination.

A problem with the prior art relates in situ measurement of fluxes at a single point. Point measurements of fluxes are extremely location dependent. Movement from one location to another produces different readings. To obtain more general readings, for example as part of an ecological or air quality study, it is required to take measurements at a large number of points and to average the resultant data, making the overall collection of data rather cumbersome.

A measurement of scintillation can give $C_n^2$, which is, in turn, sufficient information to determine heat flux for temperature fluctuations is represented by the inner scale of turbulence, denoted by $l_0$. Horizontal homogeneity means that the average quantities (as opposed to instantaneous turbulence fluctuations) are the same everywhere in a horizontal plane to within distances of several hundred times the height above ground; examples of such average quantities are heat flux, momentum flux, average wind speed, $C_n^2$, and $l_0$. For the horizontally homogeneous atmospheric surface layer there are empirical relationships between the fluxes of heat and momentum and the parameters $C_n^2$ and $l_0$. The discussion below refers to this horizontally homogeneous case.

A variety of in situ techniques are known for measuring atmospheric fluxes. The prior art methods of measuring fluxes include using a sonic anemometer or performing indirect-dissipation measurements using a fine wire thermometer and hot-film anemometers. These prior art methods, however, require excessive processing and high data rates. Also, the instruments are not particularly rugged. For example, fine-wire thermometers are subject to hygroscopic-particle contamination.

A problem with the prior art relates to in situ measurement of fluxes at a single point. Point measurements of fluxes are extremely location dependent. Movement from one location to another produces different readings. To obtain more general readings, for example as part of an ecological or air quality study, it is required to take measurements at a large number of points and to average the resultant data, making the overall collection of data rather cumbersome.

A measurement of scintillation can give $C_n^2$, which is, in turn, sufficient information to determine heat flux for the very unstable case. One of the early demonstrations of this by Wyngaard, J. C., J. C. Kaimal, G. R. Ochs, R. J. Hill and D. C. Sorensen, "An optical heat flux experiment," *Fourth Symposium on Meteorological Observations and Instrumentation*, 10–14 April, 1978, Denver, Colo., published by AMS, Boston, Mass., used a laser source. Since then, the large-aperture $C_n^2$-scintillometer has become the standard optical instrument for measuring $C_n^2$; it is far superior to using a laser source. This instrument has not been applied to measuring heat flux under very unstable conditions. This instrument is described by Wang, Ting-i, G. R. Ochs, and S. F. Clifford (1978), "A saturation-resistant optical scintillometer to measure $C_n^2$," *Journal of Optical Society of America*, Vol. 68, pp. 334–338; and Ochs, G. R. and W. D. Cartwright (1981), "An optical device for path-averaged measurements of $C_n^2$," Proc. SPIE, Vol. 277, Atmospheric Transmission, 21–22 April, 1981, Bellingham, Wash. 98227. The general possibility of measuring heat and momentum fluxes (and even humidity flux) by means of scintillation was described by Hill, R. J. and G. R. Ochs (1983), "Surface-layer micrometeorology by optical scintillation techniques," *Technical Digest, Optical Techniques for Remote Probing of the Atmosphere*, 10–12 January, 1983, Incline Village, Nev. They noted that a scintillation measurement $C_n^2$ and $l_0$ would give heat and momentum fluxes for any stability condition (i.e., unstable, near neutral, stable). The only exception is over surfaces having such great humidity flux that water vapor provides the instability rather than heat. Hill and Ochs did not foresee present methods of actually measuring $l_0$ and therefore obtaining the fluxes. Perhaps the first method for measuring $l_0$ by means of scintillation was given by Livingston, P. M. (1972), "Proposed method of inner scale measurement in a turbulent atmosphere," *Applied Optics*, Vol. 11, pp. 684–687. This method involves using laser sources and differing propagation path lengths; it has never been attempted and is probably impractical. The first attempt to use scintillation for measuring $l_0$ and $C_n^2$ used three large-aperture $C_n^2$-scintillometers having different aperture sizes; this was performed by Hill, R. J. and G. R. Ochs (1978), "Fine calibration of large-aperture optical scintillometers and an optical estimate of inner scale turbulence," *Applied Optics*, Vol. 17, pp. 3608–3612, who concluded that the accuracy was too poor to provide the fluxes of heat and momentum. Ochs, Gerard R. and Reginald J. Hill (1985), "Optical-scintillation method of measuring turbulence inner scale," *Applied Optics*, Vol. 24, pp. 2430–2432 (hereinafter referred to as "Ochs et al.") succeeded in measuring $l_0$ by using one large-aperture $C_n^2$-scintillometer in combination with a laser source and small-aperture receiver. Because of the system parameters, the $C_n^2$-scintillometer, by itself, could not provide a high-precision value of $C_n^2$, so Ochs et al. did not foresee that this basic design might be adapted to determining heat and momentum fluxes. Hill, Reginald J. (1988), "Comparison of scintillation methods for measuring the inner scale of turbulence," *Applied Optics*, Vol. 27, pp. 2187–2193, gave a theoretical comparison of the method of Ochs et al., with yet two more possible methods of measuring $l_0$. One of these two new methods, the bichromatic correlation of irradiance method, was tested experimentally by Thiermann, Volker and Ehud Azoulay (1989), "Modeling of structure constant and inner scale of refractive-index structure parameter fluctuations—an experimental investigation," Proc. SPIE Technical Symposium on Aerospace Sensing, Conf. 1115, Propagation Engineering, 27–31 March, 1989. This test gave good values of $l_0$ and $C_n^2$; they did not attempt to deduce the heat and momentum fluxes.

From the above discussion it is clear that, although there has been some theoretical discussion, a need exists in the art for a practical system for scintillation measurement of atmospheric fluxes, such as heat and momentum fluxes.

DISCLOSURE OF THE INVENTION

The primary objective of the invention is to provide an improved method and apparatus for measuring atmospheric fluxes, such as heat flux and momentum flux. More specifically, the objective is to provide more rugged flux measurement instruments and flux measurement methods which require less processing and lower data rates.

Another objective is to provide an average flux reading over a specified path length. This produces flux data which is less dependent on the location of the measuring instruments.

Another objective is to provide a practical method and apparatus for scintillation measurement of heat and momentum fluxes which will produce the desired average flux data over the length of the optical measurement path.

In its broadest form the invention is a method and an apparatus for measuring an atmospheric flux by measuring atmospheric scintillation and obtaining a flux value from the scintillation measurement.

The inventive method consists of measuring fluctuations in intensity of light received via two paths through the atmosphere and calculating a flux value from the measured fluctuations. Specifically, the fluctuation measurements are used to determine the refractive-index structure parameter. The method also determines a value for inner scale turbulence from the measured intensity fluctuations. The refractive-index structure parameter can be corrected using the inner scale of turbulence. The flux is then derived from the refractive-index structure parameter and the value of inner scale of turbulence. In preferred embodiments, the invention derives both heat flux and momentum flux using Monin-Obukhov similarity relationships.

The inventive flux meter broadly includes a scintillometer for measuring fluctuations in intensity of light received via at least one path through atmosphere and means, such as a processor, for obtaining at least one flux value from the measured intensity fluctuations. The processor derives one or more flux values such as heat flux, momentum flux or temperature flux.

The scintillometer or "inner scale meter" used to measure light intensity fluctuations incorporates a number of improvements for providing more accurate measurements. The scintillometer includes a laser light source and a detector aligned to receive light from the laser light source through the atmosphere. A source of incoherent light is aligned with a second detector. One circuit measures fluctuations in intensity of the light received from the laser light source. A second circuit measures fluctuations in intensity of the received incoherent light. The inner scale of turbulence is obtained from a ratio of the two measured variances. With the known inner scale of turbulence, the system derives the refractive-index structure parameter from one of the measured variances of intensity. Preferably a processor calculates this ratio. The processor then uses Monin-Obukhov similarity relationships to obtain the desired flux values.

In the preferred embodiment, the scintillometer measures the variance of the log intensity of the laser light detected through a 1 mm diameter aperture. The instrument measures the variance of the log intensity of the incoherent light from a 4.4 cm diameter aperture, incoherently illuminated light source. The incoherent light source detector also uses a 4.4 cm aperture. Other aperture sizes could be used.

Further objectives and advantages of the instant invention will be apparent to artisans from the drawings and the detailed description.

DETAILED DESCRIPTION OF THE PREFERRED EMBODIMENT

Figure 1:
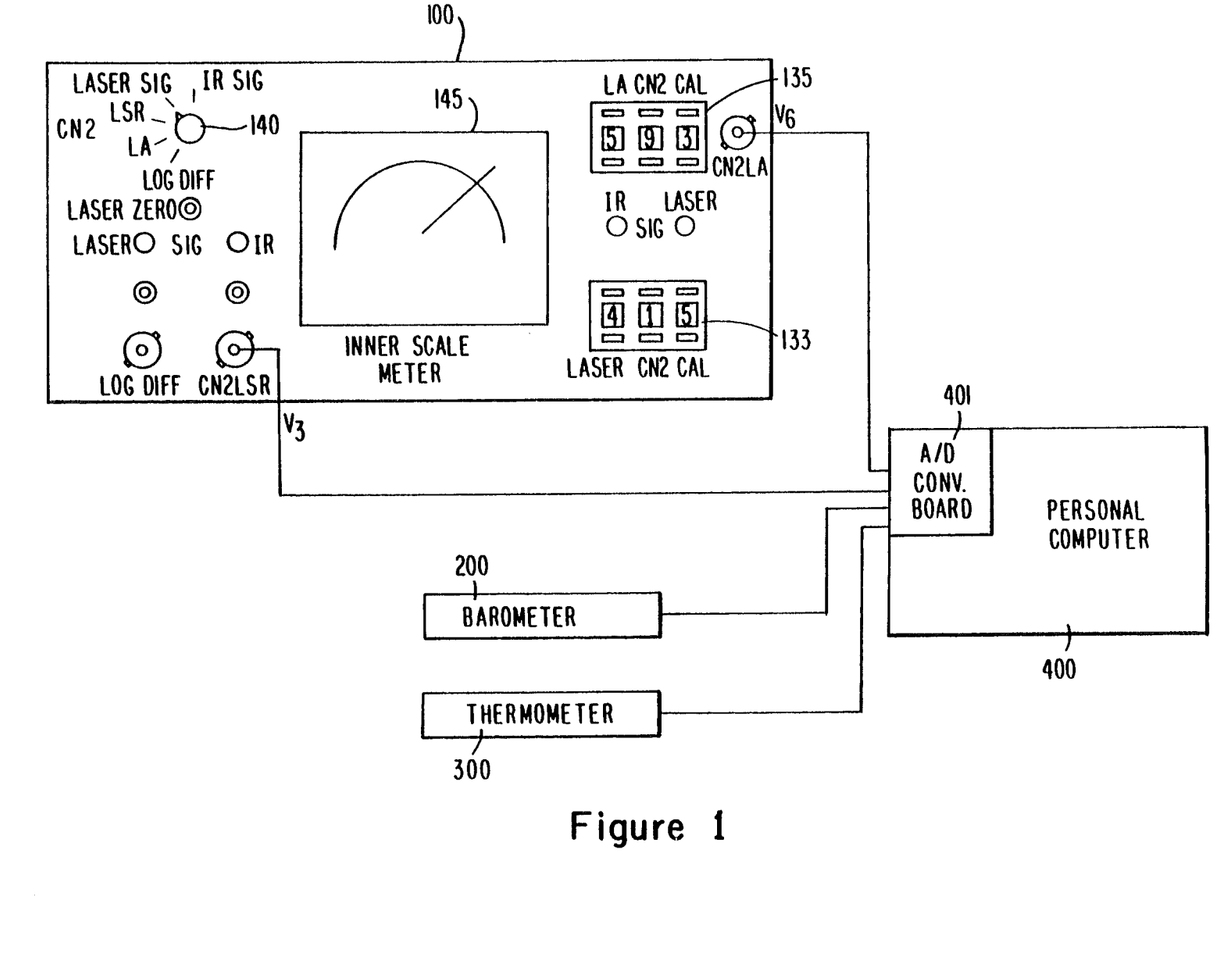
FIG. 1 is a schematic block diagram of the fluxes scintillometer of the instant invention.

As shown in FIG. 1, the fluxes scintillometer includes an inner scale meter 100, a barometer 200, a thermometer 300 and a computer 400.

As shown in FIG. 1, the computer 400 includes an analog to digital (A/D) converter board 401. The board 401 interfaces the external instruments to the computer. The A/D converter board could provide 16 single-ended or 8 differential-input channels with 12-bit resolution.

The computer 400 may be a personal computer (PC). In one experimental set up, the computer was a WIN Turbo AT, with a Data Translation series DT2801 interface board installed.

Function selector switch 140 on the face of meter 100 controls which function panel meter 145 displays. For example, when switch 140 is in the CN2 LSR position, meter 145 shows voltage $V_3$ which as discussed below is the LASER Log $C_n^2$ output. When switch 140 is in the CN2 LA position, meter 145 shows voltage $V_6$ which is the LA Log $C_n^2$ output. When switch 140 is in the LOG DIFF position, meter 145 shows voltage $V_7$ which is the difference between voltages $V_6$ and $V_3$ and corresponds essentially to the inner scale of turbulence.

The A/D converter board is not essential as other forms of data input are possible. For example, an operator could manually input readings from the inner scale meter 100 input into computer 400 using the keyboard. The barometer 200 and thermometer 300 are not essential to operation of the fluxes scintillometer, but they significantly reduce operator intervention and boost overall measurement reliability.

FIG. 1 shows the barometer 200 and the thermometer 300 connected as analog inputs to the A/D converter board 401. Any source of temperature and pressure data could be used. For example, digital devices could be directly connected to digital inputs of the PC 400 or an operator could read the data from a common household type barometer and thermometer. The type of instrumentation chosen depends on the degree of automation desired. The accuracy of the temperature and pressure data is not critical. It is even possible to use rough estimates of these values, and the resultant flux measurements will still be accurate to within 1%.

The barometer 200 should provide a reading of total atmospheric pressure P. The barometer readings typically are in millibars (mb). The programming for derivation of the flux values uses pressure in Newtons per square meter ($Nm^{-2}$). The PC 400 is programmed o convert the pressure data from mb to $Nm^{-2}$.

The thermometer 300 should provide a reading of absolute temperature T. The programming for derivation of the flux values uses temperature in degrees kelvin. If the thermometer provides the temperature data in degrees Fahrenheit or in degrees Celsius the PC can be programmed to convert the temperature data to degrees Kelvin.

Figure 2:
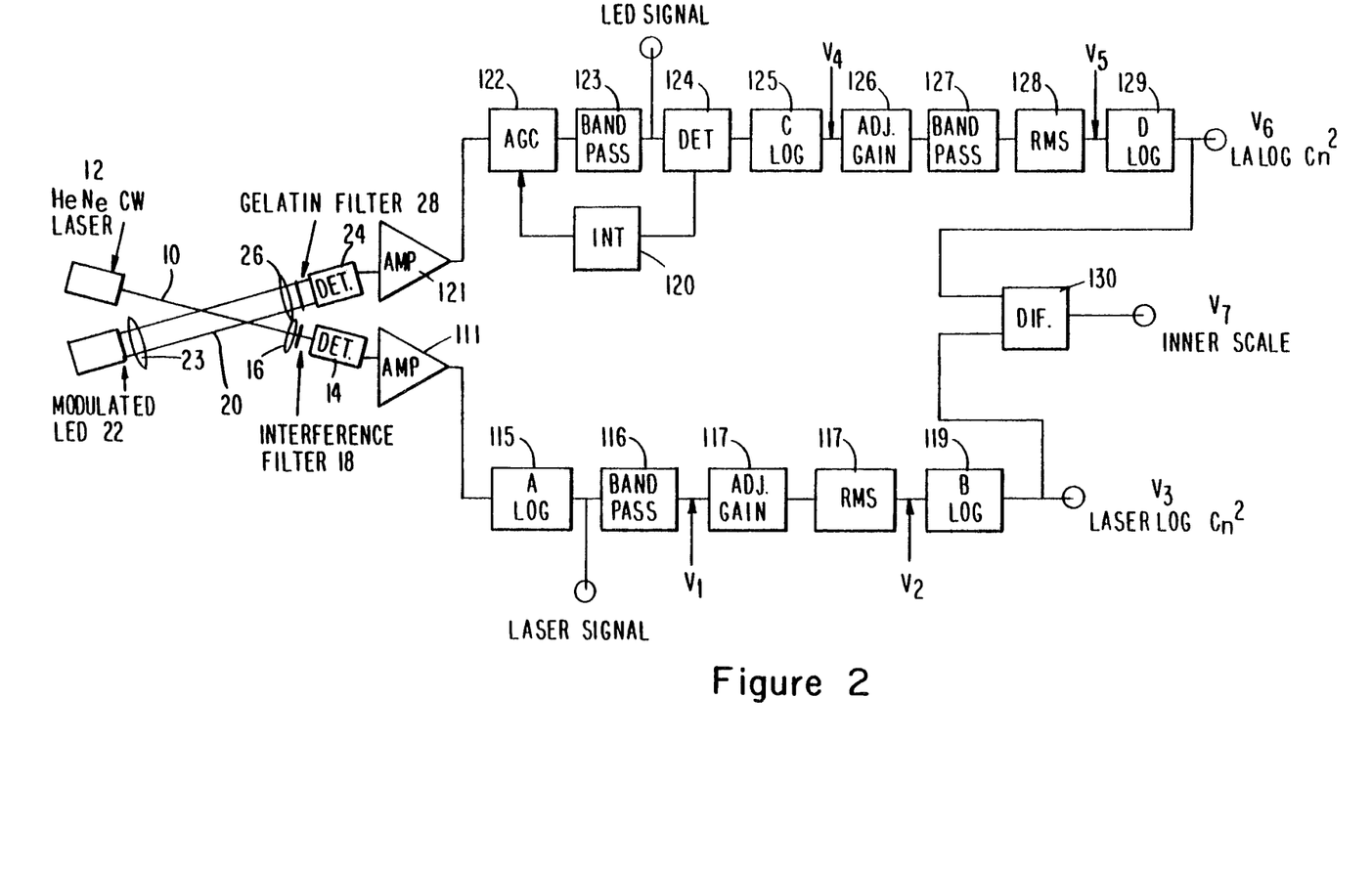
FIG. 2 is a block diagram of the circuitry and the optical measuring system of the inner scale meter used in the preferred embodiment.

FIG. 2 shows the circuitry of the inner scale meter 100. This meter 100 uses two optical paths 10 and 20 separated 14 cm at each end but crossing in the middle as shown. The 14 cm separation and the cross-over in the center are convenient, not essential. For instance, a beamsplitter at the transmitters and another beamsplitter at the receivers could make the paths coincident, but there is no advantage to doing so. Parallel rather than crossing paths could be used.

On first path 10, HeNe LASER 12 transmits continuous wave light, having a wavelength of 0.6328 micrometers ($\mu m$), to detector 14. Path 10 is the LASER path. Detector 14 receives the LASER light on path 10 through a 1 mm diameter aperture (not shown), a lens 16 and a 1 nm bandwidth interference filter 18. Interference filter 18 isolates detector 14 from background light and modulated light from the LED 22 of path 20. Detector 14 senses signal fluctuations of the continuous wave light from LASER 12.

On second path 20, LED 22 transmits modulated incoherent light through lenses 23, 26 and gelatin filter 28. Detector 24 senses signal fluctuations of the incoherent light from LED 22. In an experimental embodiment the lenses 16, 23 and 26 each comprised half of a common pair of binoculars. Lens 23 and 26 also inherently provide 4.4 cm diameter apertures.

Amplifier 111 provides a preamplification of the signal from detector 14. The first or "A" log circuit 115 takes the logarithm of the amplified detector signal. The signal then passes through bandpass filter 116. Adjustable gain circuit 117 allows calibration. Circuit 118 produces the root mean square (RMS) of the signal. The second or "B" log circuit 118 produces the logarithm of the RMS value. The result is a scaled value of the LASER log-intensity variance, log $\sigma^2_{LASER}$, which appears at the LASER Log $C_n^2$ output $V_3$. This voltage can be thought of as proportional to the logarithm of the refractive-index structure parameter structure parameter $C_n^2$ for zero inner scale. This is the calibration which would appear on the front panel of the meter and is less than the true inertial subrange $C_n^2$ for finite inner scale.

The meter observes scintillation on the second path 20 between LED 22 and detector 24. The LED 22 and detector 24 each have a 4.4 cm diameter aperture, therefore this path will be referred to as the Large Aperture (LA) path. The type TIES 16A LED 22 produces light which is square-wave modulated at 7 kHz. The light from LED 22 incoherently illuminates the transmitting aperture. Detector 24 is a 2.5 mm diameter photodiode at the focus of the objective lens 26. Gelatin filter 28, a Kodak ® 87C gelatin filter, cuts off radiation below 0.8 $\mu m$. Roll-off of the photodiode eliminates response above 1.1 $\mu m$.

Amplifier 121 provides a preamplification of the signals from detector 24. The signal from amplifier 121 passes through automatic gain control circuit AGC 122. Over its operating range, the control loop formed by AGC 122, bandpass filter 123, detector 124 and integrator 120 maintains the output signal at a constant RMS value. In a manner similar to that of the processing of the signal from LASER path 10, the signal from LA path 20 passes through a third or "C" log circuit 125, an adjustable gain circuit 126, a bandpass filter 127, an RMS circuit 128 and a fourth or "D" log circuit 129. As in the first path circuit, the adjustable gain circuit 126 allows calibration. The logarithm of the RMS value of the resulting signal appears at the LA Log $C_n^2$ output $V_6$. This output is also scaled in terms of $C_n^2$ assuming zero inner scale.

For the proper gain settings, for either the LA Log $C_n^2$ output $V_6$ or the LASER Log $C_n^2$ output $V_3$ we define the following for reference in the following:

$$CN2LSR = C_n^2, _{Laser} = 10^{(V_3-10)}$$

$$CN2LA = C_n^2, _{LA} = 10^{(V_6-10)}$$

Differencing circuit 130 produces INNER SCALE output $V_7$ from the LASER Log $C_n^2$ signal from $V_3$ and the LA Log $C_n^2$ signal from $V_6$. The resultant output therefore is $$INNER\ SCALE = LA\ Log\ C_n^2 - LASER\ Log\ C_n^2,$$

i.e., $V_7 = V_6 - V_3$.

The inner scale meter may be calibrated for a range of path lengths. A path length of 150 m is suitable for paths close to the ground, and calibration for this path length is preferred.

The transmitter and receiver assemblies should be mounted on solid vibration-free supports. Both the transmitter and receiver have rifle scopes (not shown)

used only for alignment. The field of view of the receiver is about 10 mrad. The receiver should be centered in this field of view by observing LASER and LED signal strengths on the meter. When function selector switch 140 is in the IR SIG position the meter 145 shows the strength of the signal received from LED 22 via LA path 20. When function selector switch 140 is in the LASER SIG position the meter 145 shows the strength of the signal received from LASER 12 via LASER path 10. The transmitter pointing is also important, especially that of the LASER 12, because the log-intensity variance is significantly different on the edges of the beam. One way to insure optimum pointing is to run a signal back from the receiver to the location of the transmitter. A user can check the LASER transmitter 12 by observing the received signal intensity with a voltmeter at the transmitter.

As shown in FIG. 1, the LA Log $C_n^2$ signal from $V_6$ and the LASER Log $C_n^2$ from $V_3$ go to A/D converter board 401 of PC 400. It is possible to use the INNER SCALE signal from $V_7$, but we prefer to calculate inner scale in the PC 400 using software programming. The PC 400 contains a number of programs to analyze the data from the inner scale scintillometer 100 and calculate the desired flux values.

Detailed programs used in an experimental embodiment of the invention are disclosed by J. Tant Priestley, "Data Acquisition and Analysis for the 1988 Micrometeorological Scintillation Experiment," NOAA Technical Memorandum ERL WPL-170, August 1989, and J. Tant Priestley, "An Operator's Manual for Fluxes Scintillometer Software, with Design Recommendations for an Integrated System," NOAA Technical Memorandum ERL WPL-178, March 1990. Both of the documents by J. Tant Priestly are incorporated herein by reference in their entirety. Both of these documents are available from the National Technical Information Service.

For a 150M path length, the LASER $C_n^2$ calibration is set to 640 using the digital potentiometer 133 (FIG. 1). The LA $C_n^2$ calibration is set to 196 using the digital potentiometer 135 (FIG. 1). An approximate inner scale reading may be obtained from the INNER SCALE output voltage $V_7$. One calculates $y = 10^{-V_7}$, and reads the innerscale from the table in Appendix B, of NOAA Tech. Memo. ERL WPL-178 (ibid.).

Figure 3:
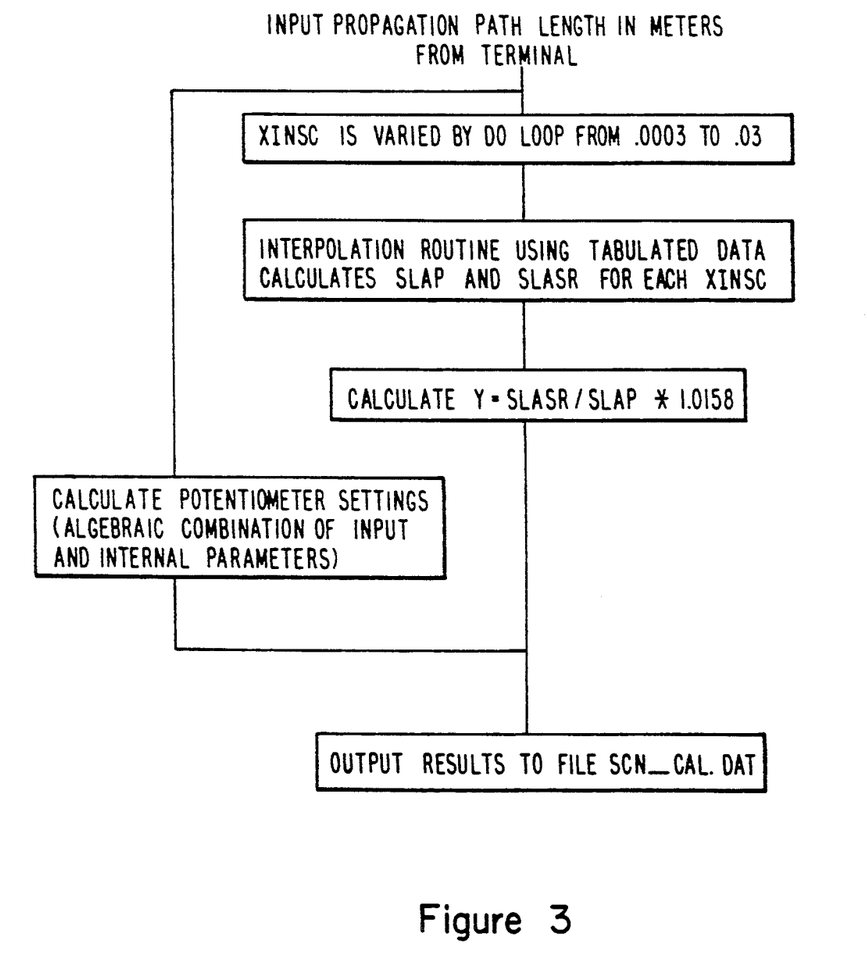
FIG. 3 and FIG. 4 are flow charts illustrating determination of fluxes from the outputs of the inner scale meter.

FIG. 3 shows the flow of program SCN_CAl used to generate a calibration data table such as shown in Appendix B of NOAA Technical Memorandum ERL WPL-178.

Figure 4:
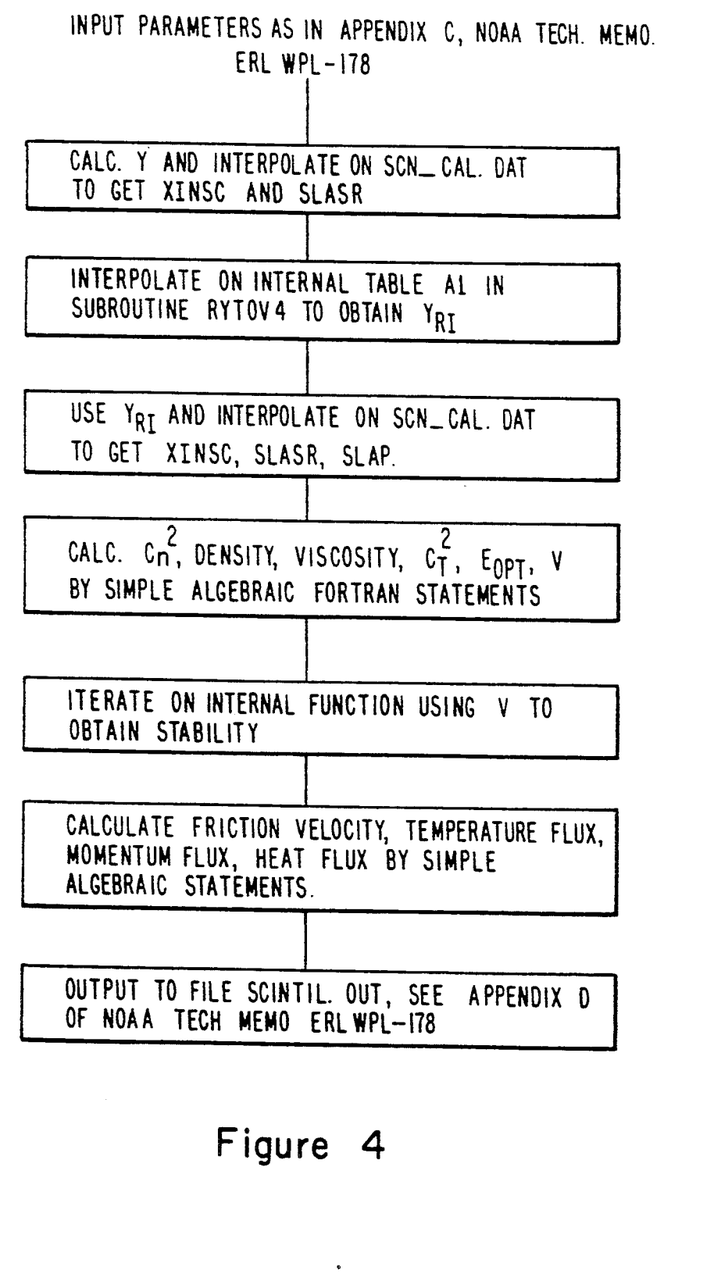

FIG. 4 is a flow chart of program SCINTL which performs the actual calculation and output of the flux values. The programming causes PC 400 to calculate fluxes in accord with the following mathematical analysis.

NOTATION: Where two symbols are used, the first is the conventional scientific symbol and the second is the FORTRAN variable name used in the processing software. Angle brackets denote a time average over the duration of the data run.

$C_n^2{}_{,LASER}$, Scaled log-intensity variance from laser CN2LSR scintillation on a path of length L having wavelength $\lambda = 0.628 \times 10^{-6}$ m and using a diverged wave, at the height $Z_H$.

$C_n^2{}_{,LA}$ Scaled log-intensity variance from a large-aperture CN2LA scintillometer of diameter $D_{LA} = 0.044$ m, on the same path, of length L and height $Z_H$, as the laser. Wavelength of radiation is $\lambda_{LA} = 0.94$ μm.

P Total atmospheric pressure in Newtons per square BARM meter (Nm$^{-2}$).
or
PBAR
T Absolute temperature from a thermometer in degrees kelvin.

The inner-scale meter has two outputs, a scaled laser variance and a scaled large-aperture-scintillometer variance. If the inner scale is zero then these scaled variances would be $C_n^2$, which is why they are sometimes referred to as "$C_n^2$". These scaled variances, which we shall designate $C_n^2{}_{,Laser}$ and $C_n^2{}_{LA}$ because their close association with $C_n^2$, are related to the log-intensity variances by $$C_{n,laser}^2 = \sigma_{Laser}^2/0.5\ k^{7/6}L^{11/6})$$
(CN2LSR)

where $k = 2\pi/\lambda$, L is propagation path length and $\lambda$ is laser radiation wavelength, and $$C_{n,LA}^2 = \sigma_{LA}^2/(0.9 D_{LA}^{-7/3} L^3)$$
(CN2LA)

where $D_{LA}$ is the diameter of the large-aperture scintillometer. The FORTRAN variables are shown in parentheses and $\sigma_{Laser}^2$ and $\sigma_{LA}^2$ are the log-intensity variances of the instruments. This scaling is provided by potentiometer settings.

Averaging the digitized values of and $C_{n,Laser}^2$ and $C_{n,LA}^2$ for as many minutes as we like, we calculate the ratio $$y = C_{n,Laser}^2/C_{n,LA}^2.$$

Using y, the table in Appendix B of NOAA Tech. Memo. ERL WPL-178 allows determination of the inner scale, $l_{opt}$ (L_OPT).

If the inner scale is zero and the saturation of scintillation is negligible, and the diverged laser beam can be approximated as initially a spherical wave, and the true refractive-index structure parameter in the atmosphere $C_n^2$, is uniform along the propagation path, then the Rytov variance of log-amplitude $\beta_0^2$, is given by $$\beta_0^2 = 0.124 k^{7/6} L^{11/6} C_n^2.$$

Now assume all of the above restrictions with the exception that the inner scale may be nonzero. To obtain the Rytov log-amplitude variance including the inner-scale effect $\sigma_R^2$, we read from appendix B (ibid.) the value of SLASR that corresponds to a given value of inner scale, then $$\sigma_R^2 = \beta_0^2 \cdot \text{SLASR}.$$

That is, for a given inner scale SLASR is the proportionality constant between $\sigma_R^2$ and $\beta_o^2$ for our experimental conditions.

We need to check the effect of saturation of scintillation on the laser variance. To do this we first calculate the log-amplitude variance $$\sigma_{\chi,Laser}^2 = 0.124 k^{7/6} L^{11/6} C_{n,Laser}^2$$

-continued (SIG2CHI)

$\sqrt{\lambda L}/l_{opt}$. With these values we use an interpolation over Table A1 to determine a value of the Rytov variance that includes inner scale effect $\sigma_R^2$. Table A1 and the interpolation routine are incorporated in subroutine RYTOV4. The data statement representing Table A1 in RYTOV4 contains some extrapolated values as well as the values in Table A1. To use Table A1 we locate the appropriate value of $\sqrt{\lambda L}/l_{opt}$ at the top and read down the column to a value that matches the value of $\sigma_{\chi,Laser}^2$ then over to the left to get a value of $\beta_0^2$. Note that for $\sqrt{\lambda L}/l_{opt} < 1.0$ one should use the column for $\sqrt{\lambda L}/l_{opt} = 1.0$. We obtain SLASR corresponding to $l_{opt}$ from Appendix B (ibid.). Then we obtain $\sigma_R^2 = \beta_0^2 *$ SLASR. If $\sigma_R^2$ differs substantially from $\sigma_{102,Laser}^2$, then we correct our ratio as follows:

$$C_{n}^2{}_{,Laser,RI} = \sigma_R^2/(0.124 k^{7/6} L^{11/6})$$

$$Y_{RI} = C_{n}^2{}_{,Laser,RI}/C_{n,LA}^2.$$

These are approximately the values that would be measured if the Rytov approximation (including the inner-scale effect) was valid for a given data run, that is, if the effects of saturation of scintillation had been negligible. The subscripts RI are a mnemonic for the words Rytov and Inner scale. Note that $C_{n}^2{}_{,Laser,RI}$ should always be greater than $C_{n}^2{}_{,Laser}$. This corrected y can be used in Appendix B (ibid.) to obtain a corrected value of the inner scale, $l_{opt,RI}$.

TABLE A1

Values of $\sigma_{\chi,Laser}^2$ for given values of $\sqrt{\lambda L}/l_{opt}$ and $\beta_0^2$

| $\beta_0^2$ \ $\sqrt{\lambda L}/l_{opt}$ | 1.0 | 2.0 | 4.0 | 7.0 | 20.0 | $\infty$ |
|---|---|---|---|---|---|---|
| 0.1 | 0.0203 | 0.0639 | 0.108 | 0.119 | 0.1035 | 0.0919 |
| 0.3 | 0.0602 | 0.183 | 0.288 | 0.302 | 0.264 | 0.241 |
| 0.6 | 0.119 | 0.342 | 0.486 | 0.480 | 0.422 | 0.397 |
| 1.0 | 0.194 | 0.523 | 0.654 | 0.607 | 0.536 | 0.523 |
| 1.5 | 0.284 | 0.704 | 0.770 | 0.668 | 0.591 | 0.601 |
| 2.0 | 0.369 | 0.848 | 0.818 | 0.687 | 0.608 | 0.629 |
| 3.5 | 0.600 | 1.105 | 0.832 | 0.673 | 0.596 | 0.627 |
| 5.0 | 0.798 | 1.210 | 0.795 | 0.655 | 0.576 | 0.597 |
| 6.5 | 0.966 | 1.245 | 0.769 | 0.645 | 0.562 | 0.575 |
| 8.0 | 1.109 | 1.231 | 0.753 | 0.635 | 0.553 | 0.559 |
| 10.0 | 1.269 | 1.191 | 0.737 | 0.627 | 0.543 | 0.542 |
| 12.0 | 1.397 | 1.147 | 0.725 | 0.619 | 0.535 | 0.534 |

We now determine $C_n^2$ from the optical inner-scale meter. The values of SLAP are obtained from Appendix B ibid.) for the determined inner scale $l_{opt}$. This means using $l_{opt,RI}$ if the saturation of scintillation was significant. From the large-aperture scintillometer the value of $C_n^2$ is $$C_{n,LA,RI,IS}^2 = C_{n,LA}^2/SLAP_{RI}$$

or from the laser scintillometer the value of $C_n^2$ is $$C_{n,LA,RI,IS}^2 = (C_n^2/SLASR_{RI})0.016$$

where the saturation-corrected inner scale, $l_{opt,RI}$, is used to find $SLAP_{RI}$ (or $SLASR_{RI}$) from the column titled SLAP (or SLASR) in Appendix B (ibid.). The coefficient 1.016 is the square of the ratio of refractivities at wavelength 0.94 μm and 0.6328 μm such that $C_n^2$ is that for wavelength 0.94 μm. With an accuracy not worse than 30%, the value of $C_{n,LA}^2$ could be used in the following in place of $C_{n,LA,RI,IS}^2$. That is, flux estimates can be obtained without using the inner scale of turbulence to obtain an accurate value of $C_n^2$, but accuracy suffers.

Finally, we determine heat and momentum fluxes from propagation statistics. There are three possible formulas for G.

(1) Wyngaard et al. (1971):

$$G(\xi) = 4.9(1 + 7.0||\xi||)^{-\frac{1}{3}} \quad \xi \leq 0$$
$$4.9(1 + 2.75\xi^{\frac{2}{3}}) \quad \xi \geq 0$$

(2) Modified Wyngaard et al. [our own fit to the data by Wyngaard et al. (1971)]:

$$G(\xi) = 8.1(1 + 15||\xi||)^{-\frac{1}{3}} \quad \xi \leq 0$$
$$2.7(1 + 5.0\xi^{\frac{2}{3}}) \quad \xi \geq 0$$

(3) Kohsiek [our own fit to the data by Kohsiek (1982) "Measuring $C_T^2$, $C_Q^2$, and $C_{TQ}$ in the unstable surface layer, and Relations to the vertical fluxes of heat and moisture," *Boundary-Layer Meteorology*, 24, pp. 89–107]:

$$G(\xi) = 17(1 + 46||\xi||)^{-\frac{1}{3}} \quad \xi \leq 0$$
$$2.7(1 + 5.0\xi^{\frac{2}{3}}) \quad \xi \geq 0$$

Kohsiek's formula for $G(\xi)$ for $\xi \geq 0$ is not known, so we take it to be the same as the Modified-Wyngaard et al. formula. All three formulas are available in the program, but we recommend using only the first.

The function h is given by Wyngaard and Coté, "The budgets of turbulent kinetic energy and temperature variance in the atmospheric surface layer," *J. Atmos. Sci.*, 28, 1971, pp. 190–201, as $$h(\xi) = (1 + 0.50||\xi||^{\frac{2}{3}})^{3/2} \quad \xi \leq 0$$
$$(1 + 2.5\xi^{3/5})^{3/2} \quad \xi \geq 0.$$

The functions $h(\xi)$ and $G(\xi)$ are the *Monin-Obukhov similarity* relations which were determined empirically by Wyngaard, J.C., Y. Izumi, and S.A. Collins, Jr. (1971): "Behavior of the refractive-index structure parameter near the ground," *J. Opt. Soc. Am.*, 61, pp. 1646–1650; and Wyngaard, J.C., and O.R. Coté (1971): "The budgets of turbulent kinetic energy and temperature variance in the atmospheric surface layer," *J. Atmos. Sci.*, 28, pp. 190–201.

$C_T^2$ is obtained from $C_{n,LA,RI,IS}^2$ using:

$$C_T^2 = C_{n,LA,RI,IS}^2 \times 10^{12} (T^2/0.78P)^2,$$

where P is the total atmospheric pressure in $Nm^{-2}$ and T is the absolute temperature from a thermometer in degrees kelvin.

The coefficient of viscosity is given by:

$$\mu = \beta T^{3/2}/((T+S)$$

where $\beta \equiv 1.458 \times 10^{-6}$ kg s$^{-1}$K$^{-\frac{1}{2}}$m$^{-1}$ and $S \equiv 110.4$ K.

The mass density of air is given by:

$$\rho = P/(287.05T).$$

The kinematic viscosity is given by:
$$\nu = \mu/\rho.$$

The energy dissipation rate, $\epsilon_{opt}$, is determined from the inner scale from the scintillometer, $l_{opt}$ (or $l_{opt,RI}$ if it is corrected for saturation of scintillation) using:

$$\epsilon_{opt} = \nu^3 (7.4/l_{opt})^4$$

We define the value $$V = g^2 K^{2/3} Z_H^{4/3} C_T^2 / \{T^2 [\epsilon_{opt}]^{4/3}\},$$

where $Z_H$ is height above ground,
$g = 9.8$ ms$^{-2}$ is the acceleration due to gravity, and
$K = 0.4$ is the VonKarman constant.

We then solve the following formula by iteration to obtain $\xi$ $$\xi^2 G(\xi)[h(\xi)]^{-4/3} = V.$$

The scintillation value of stability is then $\xi$ and the scintillation value of Monin-Obukhov length is then:

$$L_S = Z_H/\xi.$$

The scintillation values of friction velocity are:

$$u*_s = [\epsilon_{opt} K Z_H / h(\xi)]^{\frac{1}{3}}.$$

The scintillation values of temperature flux are:

$$-[T \cdot u*]_s = \frac{-\xi}{\|\xi\|} \{Z_H^{\frac{1}{3}} C_T^2 / G(\xi)\}^{\frac{1}{2}} u*_s.$$

here $C_T^2$ is the same as used above in the definition of V. The momentum flux is then:

$$\tau = -\rho(u*_s)^2,$$

and the heat flux is given by:

$$Q = \rho C \{-[T \cdot u*]_s\}$$

where $\rho$ is the mass density of air defined previously and $C = 1.00047 \times 10^{-3}$ J$^\circ$C$^{-1}$kg$^{-1}$ is the constant-pressure specific heat capacity of air. (See Sec. 2.3 of NOAA Tech. Memo. ERL WPL-178.)

The invention has been described with particular reference to preferred embodiments thereof. It will be understood, however, that modifications and variations can be made within the spirit and scope of the appended claims

The invention claimed is:

1. A flux scintillometer comprising: first means for measuring the refractive-index structure parameter of the atmosphere, wherein said first means comprise
    (i) a laser light source,
    (ii) laser light receiving means for receiving light from the laser light source through the atmosphere,
    (iii) means for measuring variance of intensity of the light received from the laser light source,
    (iv) means for correcting the measured variance of intensity of the light received from the laser light source for saturation of scintillation, and
    (iv) means for obtaining the refractive-index structure parameter of the atmosphere from the corrected measured variance of intensity of the light received from the laser light source;
    second means for obtaining a value of the inner scale of turbulence of the atmosphere;
    third means, responsive to the first and second means, for deriving at least one flux value from the refractive-index structure parameter and the inner scale of turbulence.

2. A flux scintillometer as specified in claim 1 wherein the third means derives one or more fluxes selected from the group consisting heat flux, momentum flux and temperature flux.

3. A flux scintillometer as specified in claim 1 wherein the third means derives heat flux and momentum flux.

4. A flux scintillometer as specified in claim 1 wherein the means for correcting the measured variance of intensity of the light received from the laser light source also corrects for the inner scale of turbulence.

5. A flux scintillometer as specified in claim 1 wherein the determination of the refractive-index structure parameter is also responsive to the value of the inner scale of turbulence.

6. A flux scintillometer as specified in claim 1 further comprising:
    a source of incoherent light;
    incoherent light receiving means for receiving light from the incoherent light source through the atmosphere; means for measuring variance of intensity of the received incoherent light;
    wherein said second means determines inner scale of turbulence as a ratio of the two measured variances.

7. A flux scintillometer as specified in claim 6 wherein the refractive-index structure parameter is determined in response to the measured variance of intensity of the incoherent light and the value of the inner scale of turbulence.

8. A flux scintillometer as specified in claim 6 wherein:
    the means to measure variance of intensity of laser light determines the variation of the logarithm of the intensity of the received laser light; and
    the means for measuring variance of incoherent light determines the logarithm of the intensity of the received incoherent light.

9. A flux scintillometer as specified in claim 6 wherein:
    said laser light source and said laser light receiving means are aligned along a first path through the atmosphere; and
    said source of incoherent light and said incoherent light receiving means are aligned along a second path through the atmosphere.

10. A flux scintillometer as specified in claim 1 wherein the third means derives heat flux and momentum flux from the refractive-index structure parameter and the value of the inner scale of turbulence in accordance with Monin-Obukhov similarity relationships.

11. A flux meter comprising:
    a laser light source;
    means to receive light from the laser light source through the atmosphere and to measure fluctuations in intensity of the light received from the laser light source;

means to correct the measured fluctuations in intensity of the light received from the laser light source for saturation of scintillation;

a source of incoherent light;

means to receive light from the incoherent light source through the atmosphere and to measure fluctuations in intensity of the received incoherent light; and a process or for obtaining at least one flux value in response to at least one of the corrected measured fluctuations in intensity of the light received from the laser light source and the measured fluctuations in intensity of the received incoherent light.

12. A flux meter as specified in claim 11 wherein
the laser light source and the means to receive light from the laser light source are aligned along a first path;

the source of incoherent light and the means to receive light from the incoherent light source are aligned along a second path.

13. A flux meter as specified in claim 12 wherein the first and second paths are each approximately 150 meters long.

14. A flux meter as specified in claim 12 wherein the first and second paths intersect.

15. A flux meter as specified in claim 11 further comprising:

means for deriving the refractive-index structure parameter of the atmosphere from ne of the measured fluctuations in intensity of received light;

means for obtaining a value of the inner scale of turbulence of the atmosphere as a ratio of the two measured fluctuations in intensity of received light; wherein said processor obtains said at least one flux value from the refractive-index structure parameter and the inner scale of turbulence.

16. A flux meter as specified in claim 11 further comprising:

means for obtaining a value of the inner scale of turbulence of the atmosphere as a ratio of the two measured fluctuations in intensity of received light;

means for deriving the refractive-index structure parameter of the atmosphere from the measured fluctuation in intensity of the received incoherent light and the value of the inner scale of turbulence; wherein said processor obtains said at least one flux value from the refractive-index structure parameter and the inner scale of turbulence.

17. A method of measuring atmospheric flux comprising the steps of:

measuring fluctuations in intensity of laser light received via a first path through the atmosphere;

correcting the measured fluctuations in intensity of the laser light for saturation of scintillation;

measuring fluctuations in intensity of light received via a second path through the atmosphere; and deriving a value for at least one flux from the corrected fluctuations in intensity of the laser light and the measured fluctuations form the second path.

18. A method as specified in claim 17 wherein said step of deriving a flux value comprises the steps of:

determining values for the refractive-index structure parameter from the measured intensity fluctuations; and determining a value for inner scale of turbulence from the measured intensity fluctuations; and processing the refractive-index structure parameter and the value of inner scale of turbulence to produce the flux value.

19. A method as specified in claim 18 wherein the step of deriving consists of deriving a heat flux value and a momentum flux value and said processing step applies Monin-Obukhov similarity relationships.

* * * * *